US010898438B2

(12) United States Patent
Baruzzi et al.

(10) Patent No.: US 10,898,438 B2
(45) Date of Patent: Jan. 26, 2021

(54) CAPSULE DISPENSING CONTAINER

(71) Applicant: R.P. Scherer Technologies, LLC, Las Vegas, NV (US)

(72) Inventors: Laura Baruzzi, Milan (IT); David Griffith Williams, Sr., Palm Harbor, FL (US); Arianna Provenza, Pomezia (IT); Rodrigo Fuscelli Pytel, Sao Paulo (BR)

(73) Assignee: R.P. Scherer Technologies, LLC, Las Vegas, NV (US)

( * ) Notice: Subject to any disclaimer, the term of this patent is extended or adjusted under 35 U.S.C. 154(b) by 0 days.

(21) Appl. No.: 15/587,522

(22) Filed: May 5, 2017

(65) Prior Publication Data

US 2017/0239186 A1 Aug. 24, 2017

Related U.S. Application Data

(63) Continuation of application No. 14/707,909, filed on May 8, 2015, now abandoned.

(60) Provisional application No. 62/000,615, filed on May 20, 2014.

(51) Int. Cl.
*A61K 9/48* (2006.01)
*A61J 1/06* (2006.01)
*A61J 3/00* (2006.01)
*B65D 75/58* (2006.01)

(52) U.S. Cl.
CPC ............. *A61K 9/4808* (2013.01); *A61J 1/067* (2013.01); *A61J 3/00* (2013.01); *A61K 9/4816* (2013.01); *A61K 9/4825* (2013.01); *A61K 9/4833* (2013.01); *A61K 9/4883* (2013.01); *B65D 75/58* (2013.01); *B65D 2221/00* (2013.01)

(58) Field of Classification Search
CPC .................................................... A61K 9/4808
USPC ........................................................ 424/452
See application file for complete search history.

(56) References Cited

U.S. PATENT DOCUMENTS

| | | |
|---|---|---|
| 1,970,396 A | 8/1934 | Scherer |
| 2,134,389 A | 10/1938 | Gessler |
| 2,288,327 A | 6/1942 | Scherer |
| 2,397,051 A | 3/1946 | Scherer |
| 2,552,870 A | 5/1951 | Scherer |
| 2,580,414 A | 1/1952 | Duffey |
| 2,630,238 A | 3/1953 | Battersby |
| 2,663,461 A | 12/1953 | Brown |
| 3,216,562 A | 11/1965 | Lockwood |
| 4,215,104 A | 7/1980 | Ullman et al. |
| 4,780,316 A | 10/1988 | Brox |
| 5,063,057 A | 11/1991 | Spellman et al. |
| 5,270,054 A | 12/1993 | Bertolini |
| 5,380,534 A | 1/1995 | Schurig et al. |
| 5,422,160 A | 6/1995 | Ratko et al. |
| 5,535,885 A | 7/1996 | Daniel et al. |
| 5,614,217 A | 3/1997 | Chiprich et al. |
| 5,827,535 A | 10/1998 | Stone |
| 6,007,264 A | 12/1999 | Koptis |
| 6,280,767 B1 | 8/2001 | Sane et al. |
| 6,315,480 B1 | 11/2001 | Martel et al. |
| 6,823,649 B1 | 11/2004 | Pauchet |
| 7,757,893 B2 | 7/2010 | Perell |
| 8,151,984 B2 | 4/2012 | Braeder et al. |
| 2003/0019781 A1 | 1/2003 | Kocher |
| 2008/0057115 A1 | 3/2008 | Okamoto et al. |
| 2009/0208568 A1 | 8/2009 | Hanneted et al. |
| 2010/0059402 A1 | 3/2010 | Burattini |
| 2011/0097397 A1 | 4/2011 | Wang et al. |
| 2012/0087978 A1 | 4/2012 | Nause |
| 2014/0299625 A1 | 10/2014 | Franco Soutello et al. |
| 2015/0335586 A1* | 11/2015 | Baruzzi ................ A61K 9/4808 424/452 |

FOREIGN PATENT DOCUMENTS

| | | |
|---|---|---|
| CN | 101039852 A | 9/2007 |
| EP | 0543406 A1 | 5/1993 |
| EP | 0673213 | 9/1995 |
| EP | 0743057 A2 | 11/1996 |
| EP | 1496871 B1 | 9/2008 |
| EP | 1898889 B1 | 10/2009 |
| EP | 2170727 B1 | 8/2012 |
| JP | H08502663 A | 3/1996 |
| JP | H08502672 A | 3/1996 |
| JP | 2006034416 A | 2/2006 |
| JP | 2006299052 A | 11/2006 |

(Continued)

OTHER PUBLICATIONS

European Office Action; dated Jun. 22, 2018 for EP Application No. 15 796 874.4.
Chinese Office Action; dated Sep. 30, 2018 for CN Application No. 201580026164.4.
Supplementary European Search Report; dated Nov. 14, 2017 for EP Application No. 15796874.
Chinese Office Action; dated Feb. 26, 2018 for CN Application No. 201580026164.4.

(Continued)

*Primary Examiner* — Devang K Thakor
(74) *Attorney, Agent, or Firm* — Mendelsohn Dunleavy, P.C.

(57) ABSTRACT

A package for delivering a single-dose product includes a softgel capsule which is comprised of at least one gelling agent selected from protein-based gelling agents and polysaccharide-based gelling agents. The capsule shell includes one or more areas of reduced thickness that are preferentially ruptured by exertion of a compressive force on the softgel capsule to create an opening in the capsule shell through which the fill composition can be delivered by spraying or squeezing. A method for manufacturing the softgel capsule having one or more areas of reduced shell thickness is also described.

17 Claims, 3 Drawing Sheets

(56) References Cited

FOREIGN PATENT DOCUMENTS

| WO | WO9414356 A1 | 7/1994 |
|----|---|---|
| WO | WO9842294 A1 | 10/1998 |
| WO | WO2006136196 A1 | 12/2006 |
| WO | WO2006136198 A1 | 12/2006 |
| WO | WO2007145535 A2 | 12/2007 |
| WO | WO2011086331 A2 | 7/2011 |

OTHER PUBLICATIONS

"Vegicaps Capsules: An Innovative Solution for Encapsulation Challenges," Retrieved on Aug. 21, 2015 from: http://www.catalent.com/index.php/content/download/1246/15111/file/Catalent_Vegicaps_Info.pdf.

Agrawal, S. S., et al. "Dr. Bhawna Bhatt Delhi Institute of Pharmaceutical Science and Research Sector-3, Pushp Vihar New Delhi." (2007).

International Search Report; dated Aug. 18, 2015 for PCT Application No. PCT/US2015/030126.

American Heritage Dictionary (https://ahdictionary.com/word/search.html?q=thickness&submit.x=54&submit.y=29; accessed Feb. 5, 2017).

Taiwan Office Action; dated Jan. 16, 2019 for TW Application No. 104115072.

Examination Report from corresponding Indian application No. 201617037361; dated Feb. 20, 2020 (6 pages).

1st Substantive Examination for corresponding Mexican application No. MX/a/2016/015184; dated Jan. 30, 2020 (5 pages).

Notice of Reasons for Refusal for corresponding Japanese Patent Application No. 2016-565049; transmittal date May 14, 2019.

Technical Report for corresponding Bolivian Application No. SP89-2015; dated Mar. 15, 2019.

\* cited by examiner

100

100

CAPSULE DISPENSING CONTAINER

RELATED APPLICATION DATA

This application is a continuation of U.S. patent application Ser. No. 14/707,909, filed May 8, 2015, which claims priority to U.S. Provisional Application No. 62/000,615, filed May 20, 2014, the entire disclosure of which is hereby incorporated by reference as if set forth fully herein.

BACKGROUND OF THE INVENTION

1. Field of the Invention

The present invention relates to single-dose capsules. In particular, the invention is directed to softgel capsules with at least one area of reduced thickness for delivering the content in the softgel capsule as a single-dose by squeezing and/or as a spray.

2. Description of the Related Technology

In the field of perfumery and cosmetics, it is common practice to distribute to the public free samples which contain a single-dose of the product in order to offer a chance to try the product. In addition, nutritional supplements or pharmaceutical agents in liquid carriers are also often distributed in single-dose containers. These single-dose forms have many advantages over other dosage forms such as bulk liquid preparations. For example, the content in a single-dose form can be individually fully identifiable and the integrity of the dosage form is protected until the actual moment of administration. If the content, e.g. cosmetics, nutritional supplements, pharmaceuticals, etc., is not used and the container is intact, the container may be retrieved and used with its integrity preserved.

Furthermore, supplying a pharmaceutical agent in a single-dose container permits accurate delivery of a unit dose. This is an advantage which becomes especially important when relatively small amounts of the pharmaceutical agent must be delivered, as in the case of certain hormones. Such uniformity is more difficult to achieve via a tableting process where solids must be uniformly mixed and compressed, or via incorporation of the total dose of active ingredient into a bulk liquid carrier which then requires precise measurement of each dose prior to each administration.

Single-dose cosmetics, nutritional supplements, or pharmaceuticals are traditionally packaged in small bottles with a removable stopper, with a spray device, or in sachets with a tearable tab or with a line of weakness for delivering these products. U.S. Pat. No. 6,315,480 discloses a device for diffusing a fluid product dose contained in a sealed reserve defined by an envelope made of a flexible and ductile material, such that a collapsing pressure applied on the reserve causes the envelope to burst open releasing the product contained in the reserve. The envelope is locally provided with an area of reduced thickness forming a pre-opening, so as to cause the envelope to burst open at the pre-opening, thereby channeling the product through the pre-opening in a predetermined direction. The flexible and ductile material may be plastic. The device is applicable for delivery of a pharmaceutical, cosmetic, food, hygiene, perfume, or household-cleaning products. The area of reduced thickness may have perpendicular lines allowing the product to be sprayed out.

WO 2007/145535 discloses a sachet that can be opened by application of a compression force to form an opening in the package at a line of weakness. The publication teaches that various mechanisms are known to aid in control of the rupturing and dispensing process and that typically at least one web is made from a relatively stiff or semi-rigid material which has a region that is weakened by a cut or a pattern of cuts or other zones of weakness. The line of weakness may be produced by making a cut in the material to create a thinner portion of the material at the line of weakness compared to adjacent portions of the material of the package.

U.S. Pat. No. 6,007,264 discloses a small sized shallow pouch-like container for a dispensable ingredient that includes a pair of built-in outwardly pivotable flaps positioned on opposite sides of the container's outlet end to form a package applicator. Squeezing the container's sides with the fingers expresses the stored ingredient through the outlet and onto the applicator flaps. Using the container portion as a finger grip, the flaps may be moved about the desired surface, spreading the dispensed ingredient. In a preferred embodiment, the container and applicator combination is formed by a pair of flexible foil sheets of substantially identical structure that are superimposed over one another and partially connected together to define both the container and the applicator. The container may be made from a thermoplastic material and can be used for holding perfume and other cosmetics.

U.S. Pat. No. 5,270,054 discloses a capsule for storing a cosmetic composition. The capsule has a spheroidal body with a hollow chamber forming a major portion of the capsule, a tab connected with the major portion by a neck section, which may be broken upon twisting to release the cosmetic composition from the hollow chamber. The opened capsule may be gently squeezed to force the stored cosmetic composition out of the punctured opening. The capsule may be a softgel capsule made from gelatin selected from Type A, Type B or a combination thereof. The amount of cosmetic composition held in the capsule ranges from about 0.05 to about 5 grams, or from about 0.3 to about 2 grams.

U.S. Pat. No. 5,380,534 discloses a soft gelatin capsule with knurled surfaces on the shell to enhance gripping and manipulation of the capsule. Besides gelatin, the soft gelatin capsule also comprises a starch or starch derivative, as well as a thickener (such as carrageenans). In one embodiment, the soft gelatin capsule shell comprises acylated gelatin, high amylose starch, and glycerol. The soft gelatin capsule comprises a removable tab integrally formed with the main portion of the capsule to seal the capsule. The neck portion connecting the removable tab and the main portion of the capsule can be easily broken by twisting off the tab. The contents of the capsule may then be dispensed by squeezing the capsule.

U.S. Pat. No. 5,063,057 discloses a capsule for packaging a cosmetic product. The capsule has a round body with a hollow chamber and a tab connected with the hollow chamber by a neck section. The tab may be removed by twisting and breaking the neck section to allow release of the cosmetic product. The capsule may be made from a soft gelatin gel. The amount of cosmetic product held in the capsule ranges from about 0.05 to about 5 grams, or from about 0.3 to about 2 grams.

U.S. Pat. No. 6,280,767 discloses a soft gelatin capsule of the torsional opening type made of gelatin, one or more plasticizers, and a water-insoluble cellulose. The soft gelatin capsule has an elongated body comprising a narrow rupture portion. The soft gelatin capsule can be twisted open with the fingers at the rupture portion by application of a torsional force thereto.

WO 1994/014356 discloses a sample container comprising a central cosmetic-containing portion substantially surrounded by a peripheral portion with thickened edges. The central portion is preferably made of a soft gelatin, while the thickened edges may be made of a solid gelatin. In a preferred embodiment, the container is made of soft gelatin. A narrowed neck portion connects the central cosmetic-containing portion to a tab, removal of which provides access to the cosmetic product in the central cosmetic-containing portion. The central cosmetic-containing portion is preferably cylindrical or an oblong cylindrical shape. According to WO 1994/014356, the cosmetic in the container may be perfumes, lotions, or creams.

These single-dose containers often need to be opened by tearing or twisting using one's hands. Such containers may be difficult to handle for some people in that they require two hands to open. In addition, many such containers that provide sprayable delivery are not biodegradable while many containers that are biodegradable do not provide sprayable delivery, which is advantageous for many applications.

Thus, one objective of the present invention is to eliminate the aforementioned drawbacks of present single dose containers, and to provide a container for delivering a single-dose of a fluid product. In various aspects of the invention a container is provided that is simple to use, inexpensive to manufacture, completely biodegradable, effective in operation, compact, and lightweight Also, in some embodiments, the container of the present invention provides the ability to spray the product out of the container to permit application of the product by spraying over an area. This feature is particularly advantageous for dispensing of cosmetics, cleaning products or other products that are intended to be spread over an area for use. More particularly, the single-dose container of the present invention may comprise an area of reduced thickness, which bursts when the container is compressed. The content within the container may thus be sprayed or squeezed out to an intended location.

SUMMARY OF THE INVENTION

In one aspect, the present invention provides a softgel capsule package for delivering a single-dose product. The softgel capsule package includes a softgel capsule shell (5) formed from at least one gelling agent selected from a protein and a polysaccharide. The softgel capsule shell (5) includes at least one area having a first shell thickness, and one or more areas of reduced shell thickness configured to preferentially rupture by exertion of a compression force on the softgel capsule shell (5) to provide an opening in the capsule shell (5) through which a fill contained in the package (100) can be dispensed.

In another aspect, the present invention provides a method for manufacturing the softgel capsule package. The method includes providing a fill composition between two pieces of softgel material, fusing the two pieces of softgel material to form a softgel capsule encapsulating the fill composition; and creating at least one area of reduced thickness (3) on a capsule shell (5) of the softgel capsule prior to or during said fusing step.

In one aspect, the invention provides a softgel capsule package that can be opened by squeezing and the contents of the package can also be dispensed by squeezing.

In a further aspect, the invention provides a softgel capsule package that can be opened by squeezing and the contents of the package can be dispensed in the form of a spray by exertion of a compressive force on the package.

DETAILED DESCRIPTION OF THE PREFERRED EMBODIMENT(S)

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in, other systems and methods. Before explaining the disclosed embodiments of the present invention in detail, it is to be understood that the invention is not limited in its application to the details of any particular embodiment shown. Additionally, the terminology used herein is for the purpose of description and not for limitation. Furthermore, although certain methods are described with reference to steps that are presented herein in a certain order, in many instances, these steps can be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more", and "at least one" can be used interchangeably herein. The terms "comprising", "including", "having" and "constructed from" can also be used interchangeably.

Figure 1:
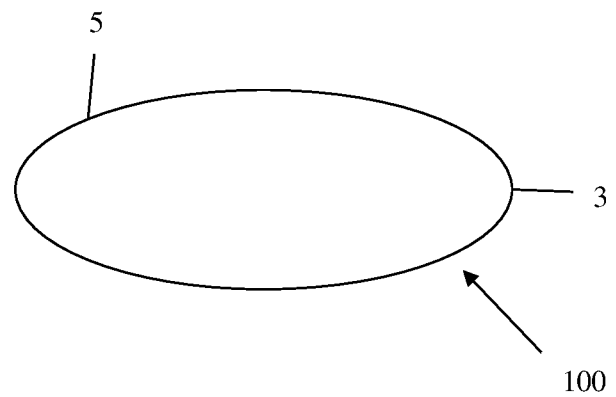
FIG. 1 is a schematic representation of a softgel capsule according to one embodiment of the present invention.

In one aspect, the present invention provides a package 100 for delivering a single-dose product as shown in FIG. 1. The package 100 includes a capsule shell 5. The capsule shell 5 includes one or more areas of reduced thickness 3 that enable opening of the package 100 by compressing the package 100 to cause rupture of the capsule shell 5 at the one or more areas of reduced thickness 3. A fill contained in the package 100 can be reliably dispensed from the package 100 via the one or more ruptured areas of reduced thickness 3 by being sprayed or squeezed out of the capsule shell 5 to an intended dispensing location.

The capsule shell 5 of the package 100 is impermeable to the fill therein, but could be permeable to other solvents, such as water. The package 100 provides a single-dose product and thus is small in size. The volume of the package 100 may be from about 0.05 to about 5 ml, or from about 0.1 to about 3 ml, or about 0.2 to about 2 ml, or about 0.25 to about 1 ml.

The package 100 may have a variety of shapes including common shapes such as spheres, oblong shapes, elongated tubes, disks, squares, rectangles, cylindrical shapes, ellipsoidal shapes, cat ear shapes or other geometrical shapes. The package 100 may also have shapes that are customized for a specific product or vender, such as sports mascots, logos, sporting goods, and likenesses of animals and humans, or portions thereof.

The one or more areas of reduced thickness 3 may be located anywhere on the capsule shell 5. In some embodiments, the area of reduced thickness will be offset from the center of the capsule shell 5 to provide a large portion of the capsule shell 5 that can be compressed to rupture the area of reduced thickness 3. In some embodiments, the area of reduced thickness 3 is located at an end or a corner of the package 100 where the package 100 has an end or a corner (such as rectangular shape or spheroidal shape, FIG. 1). In some embodiments, two areas of reduced thickness 3, or three areas of reduced thickness 3, or four or more areas of reduced thickness, may be provided as a cluster on the capsule shell 5. The plurality of areas of reduced thickness 3 may be used to provide a spray of a plurality of streams of the fill when dispensed from the package 100 that might be useful when spreading the fill over an area is desired.

Figure 3A:
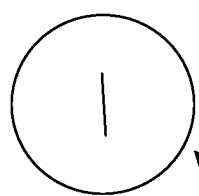
FIGS. 3A-3B show different embodiments of areas of reduced thickness on softgel capsules as viewed from the right side of FIG. 1.
Figure 3B:
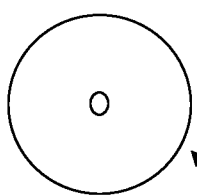
Figure 3C:
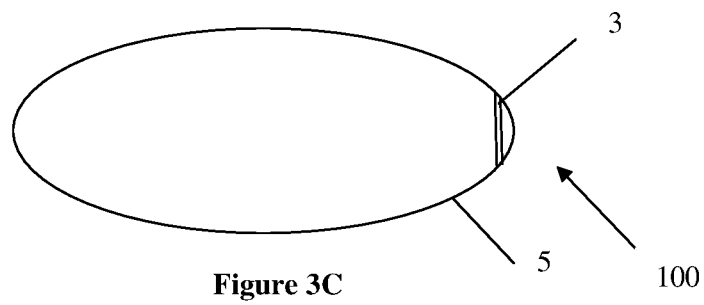
FIG. 3C shows an area of reduced thickness on a softgel capsule with the area of reduced thickness circumscribing a portion of the softgel capsule.
Figure 3D:
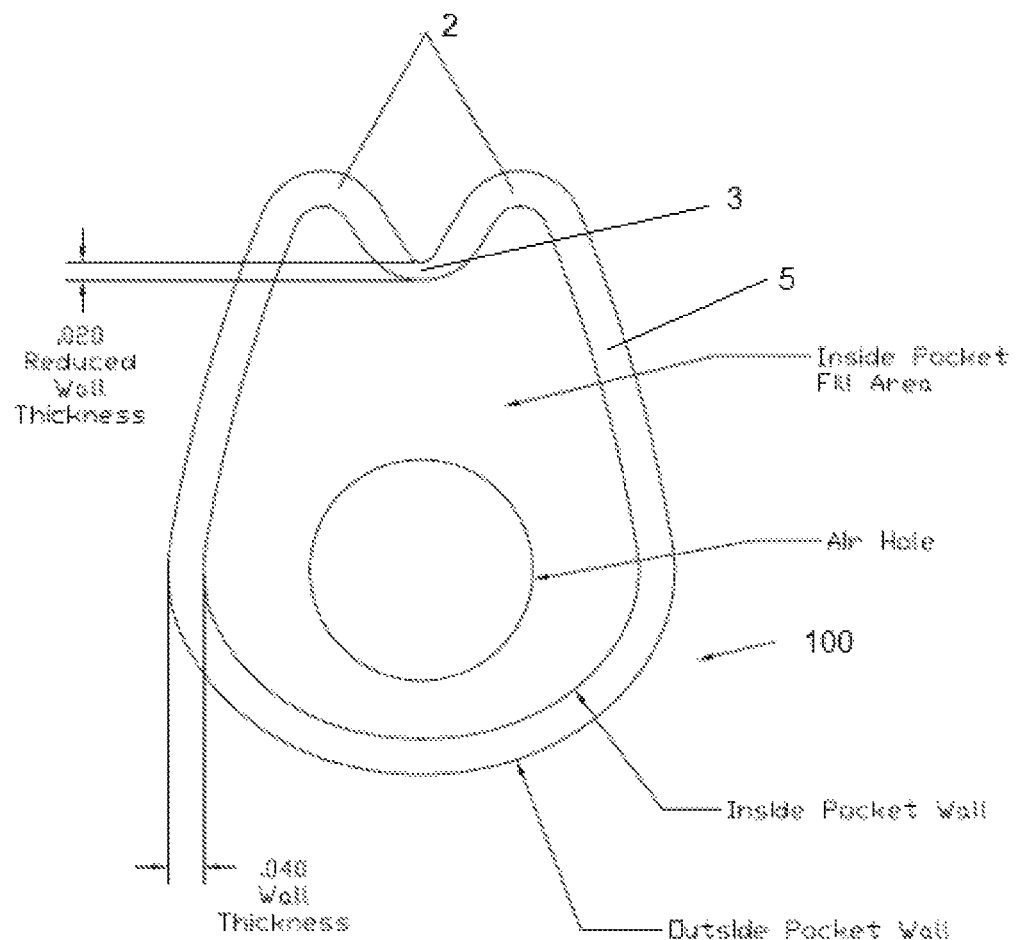
FIG. 3D shows an embodiment of softgel capsule that has two protrusions and wherein the area of reduced thickness is located between the two protrusions (cat ear shape).

The cat ear shape package 100 of FIG. 3D may include an air hole located in a central area of the package 100. In a preferred shape, the area of reduced thickness 3 is a decreased land or surface area bounded by two protrusions 2 such as in the cat ear shape shown in FIG. 3D. The land or surface area is decreased in the sense that the protrusions 2 define borders of the land or surface area within which the area of reduced thickness 3 may be located, thereby decreasing the potential size of an opening created by exerting pressure on the area of reduced thickness 3, relative to a similar package without the protrusions 2. These two protrusions 2 stabilize the fill material in the capsule and create a back pressure directly on the area of reduced thickness 3. The pressure may rupture the area of reduced thickness 3 to express the fill material. The area of reduced thickness 3 also provides a specific start point for the expression, as well as fanning the fill material between the two protrusions 2.

The walls of the package may be shaped, as shown in FIG. 3D, to help direct compressive force applied to the package 100 to the area of reduced thickness 3 to facilitate both opening the package 100 and dispensing of the contents of the package 100, particularly for spray dispensing.

The area of reduced thickness 3 may be a dot, a line, or multiple lines that are parallel or intersecting as shown in FIGS. 3A-3D. In some embodiments, the area of reduced thickness 3 may have a shape such as fantasy shapes, animals, flowers, a sun, other natural patterns or portions thereof, preferably located in a decreased land area between two protrusions 2, where the two protrusions 2 have the shape of, for example, ears, tails, hands, noses and the like. The area of reduced thickness may be of different lengths or widths in order to customize the rate or pattern of dispensing of the fill from the package 100.

The area of reduced thickness 3 is more fragile than the remainder of the capsule shell 5 and thus will be preferentially ruptured when a sufficient compression force is applied to the package 100. The pressure may be applied via hand or finger pressure such as by squeezing the package. The pressure may also be applied by a device designed for use with the package of the invention such as a home deodorizer or similar small appliances provided with structure that can exert a compressive force on the package 100. The appliances may be able to squeeze the package 100 following an established rhythm/path to provide the desired dispensing from package 100.

The ruptured area of reduced thickness 3 becomes an ejection orifice for the fill of the package 100 which provides a channel through capsule shell 5 for dispensing the fill. The fill may be dispensed as a spray and/or by squeezing the fill from the package 100 in a predetermined direction. The fill may be sprayed or squeezed onto the intended location of use.

In one embodiment, the package 100 may be in the form of an oblong/tear shape. In this embodiment, the application of pressure on the sides where the sealing line resides provides an excellent spray effect. In addition, this embodiment is easy to use and facilitates control of the spray effect. The extended radius on each side of the break point causes the fill material to find the center location during application of pressure. The area of reduced wall thickness 3 enhances the break and allows fill material to express at the center point. The area of reduced thickness 3 may be sized to provide a desired dispensing such as a fine spray.

Figure 2:
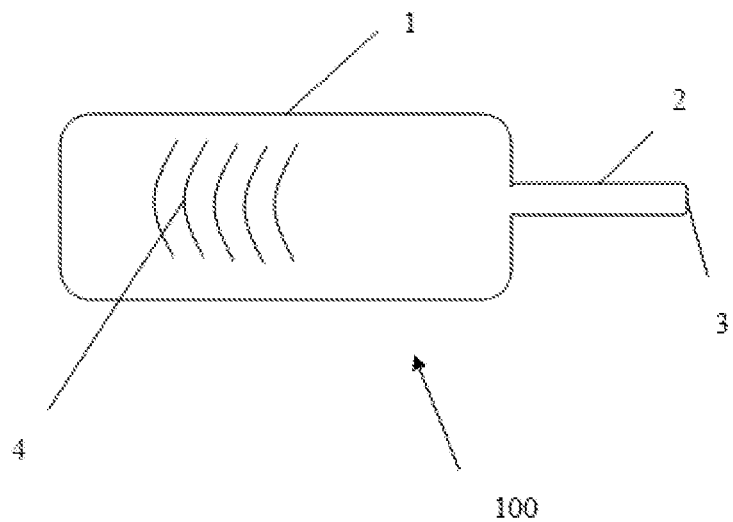
FIG. 2 is a schematic representation of a softgel capsule with a protrusion, according to one embodiment of the present invention.

In some embodiments, the package 100 may have a main body 1 and a protrusion 2 as shown in FIG. 2. The main body 1 may have any shape such as a shape of a sphere, a spheroidal shape, an ellipsoidal shape, a rectangular shape, a cylindrical shape or a cubic shape. The protrusion 2 extends, preferably radially outwardly, from the main body 1. The protrusion 2 may be any shape such as a bulge, a cylindrical protrusion, a finger-like shape, or in the form of a likeness of an ear, tail, hand, nose, and the like. In some embodiments, the protrusion 2 may extend less than about 0.5 mm, or less about 0.4 mm, or less than about 0.3 mm, or less than about 0.2 mm from the main body 1.

The area of reduced thickness 3 may be located on the protrusion 2. The user can compress the main body 1 of package 100 in order to rupture the area of reduced thickness 3 on the protrusion 2. Placing the area of reduced thickness 3 on the protrusion 2, at the tip or in a decreased land area of protrusion 2, may offer convenience for dispensing the fill to certain locations such as inside of the ears, nose, or mouth. The protrusions help direct the fill to flow to the location of the area of reduced thickness 3 in order to facilitate dispensing and, in some embodiments, to help focus the exertion of pressure on the area of reduced thickness 3 to facilitate opening the package 100.

In some embodiments, a plurality of protrusions 2 may be present on the package 100 each with an area of reduced thickness 3. In some embodiments, the package 100 has two protrusions 2 where the area of reduced thickness 3 is located in a decreased land area between the two protrusions 2. The plurality of protrusions 2 may form a cluster on the package 100. In some embodiments, plurality of protrusions 2 with plurality of areas of reduced thickness 3 may provide a plurality of dispensing streams when it is desirable to spray the fill out of the package 100 over a relatively large area, for example for perfumes or deodorants.

Optionally, at least a portion of the surface of the capsule shell 5 may be textured by providing textured areas 4 as shown FIG. 2. The texturing may be provided by, for example, a raised pattern on the surface of the package 100 such as ridges, stripes, bars, bands, streaks, strips, spots, striations, ribs, and combinations thereof, and combinations thereof. This texturing can be applied to capsule shells that comprise gelatin. The texturing may also be provided by one or more indentations in the surface of the package 100 of any suitable size or shape though care must be taken not to create an area of weakness that could rupture during compression. A user may hold and compress the package 100 at the textured areas 4 for ease of handling and/or to improve grip on the package 100 during compression of the package 100 for dispensing. The texture 4 is preferably imparted to the package 100 during the manufacturing process by, for example, use of a die that provides texture to the film used to form the capsule shell 5.

The softgel capsule shell 5 of the package 100 is formed from at least one gelling agent. In some embodiments, the softgel capsule shell 5 may be formed from a combination of two gelling agents. The gelling agents of the present invention may be selected from protein-based gelling agents and polysaccharide-based gelling agents.

Protein-Based Gelling Agents

The protein-based gelling agent may be selected from collagen, egg whites, gelatin, or milk-based proteins. "Collagen" refers to a protein of connective tissue in animals. "Gelatin" refers to a translucent, colorless, odorless, brittle, nearly tasteless solid protein substance, derived from the collagen by partial hydrolysis. Generally, gelatin is classified into alkaline gelatin, acidic gelatin, or enzymatic gelatin. Alkaline gelatin is obtained from the treatment of collagen with a base such as calcium hydroxide. Acidic gelatin is obtained from the treatment of collagen with an acid such as hydrochloric acid. Enzymatic gelatin is generated from treatment of collagen with a hydrolase. Gelatin is commonly used as a gelling agent in food, pharmaceuticals, photography, and cosmetic manufacturing. In the context of the present invention, "gelatin" also includes substantially equivalent substances such as synthetic analogues of natural gelatin.

Polysaccharide-Based Gelling Agents

The gelling agent of the present invention may also be polysaccharide-based. The polysaccharide-based gelling agents are commonly derived from a plant source, such as starch or cellulose. The polysaccharide-based gelling agent may be selected from cellulose or cellulose derivatives, such as microcrystalline cellulose, sodium carboxymethyl cellulose, methylcellulose, ethyl cellulose, hydroxyethyl cellulose, hydroxypropyl cellulose, and hydroxypropyl methylcellulose, starch and starch derivatives, pectin, gum, dextrins, alginates and carrageenans. Exemplary starches include arracacha starch, arrowroot starch, banana starch, barley starch, breadfruit starch, buckwheat starch, canna starch, cassava starch, colacasia starch, corn starch, katakuri starch, kudzu starch, malanga starch, millet starch, oat starch, oca starch, pea starch, polynesian arrowroot starch, potato starch, rice starch, rye starch, sago starch, sorghum starch, sweet potato starch, taro starch, water chestnut starch, wheat starch, yam starch, and mixtures thereof.

The starch of the present invention may be a modified starch. The term "modified starch" refers to derivatives prepared by chemical treatment of starches, for example, acid treatment starches, enzyme treatment starches, oxidized starches, cross-bonding starches, and other starch derivatives. It is preferred that the modified starches be derivatized where their side chains are modified with hydrophilic or hydrophobic groups to thereby form a more complicated structure with a stronger interaction between side chains comparing with unmodified starches. Exemplary modified starch ethers and esters include carboxymethylated starch, hydroxypropylated starch, and hydroxypropylated carboxymethyl crosslinked starch.

"Modified starch ester" refers to a starch in which one or more of the hydroxyl groups have been reacted to form ester groups. The reaction usually involves a reaction to replace the hydrogen of the OH group on the starch with a —O—(C=O)—CH$_3$ or —O—(C=O)—R group (where R is an aliphatic group).

"Modified starch ether" refers to a starch in which one or more of the hydrogens on the starch has been replaced by the carbon of an organic groups. For example methylation of a starch replaces the OH group with an OCH$_3$ group.

Gum

The polysaccharide-based gelling agent of the present invention may also be a gum. Exemplary gums include acacia gum, agar, carrageenans, cassia gum, cellulose gum, furcellaran, gellan gum, guar gum, gum ghatti, karaya gum, larch gum, locust bean gum, pectin, plantago, tara gum, tragacanth, xanthan gum, or a combination thereof.

"Gum" refers to polysaccharides of natural origin, capable of causing a large viscosity increase in solution, even at small concentrations. They are used as thickening agents, gelling agents, emulsifiers, and stabilizers. Most often, these gums are found in the woody elements of plants or in seed coatings.

Pectin

The polysaccharide-based gelling agent of the present invention may be pectin. "Pectin" refers to the complex set of polysaccharides that are present in most primary cell walls and particularly abundant in the non-woody parts of terrestrial plants. The characteristic structure of pectin is a linear chain of α-(1-4)-linked D-galacturonic acid that forms the pectin-backbone, a homogalacturonan. Into this backbone, there are regions where galacturonic acid is replaced by (1-2)-linked L-rhamnose. From the rhamnose residues, side chains of various neutral sugars branch off.

The pectin of this invention include not only purified or isolated pectates, but also crude natural pectin sources, such as apple, citrus or sugar beet residues which have been subjected, when necessary, to esterification or de-esterification, e.g., by alkali or enzymes. Preferably, the pectins used in this invention are derived from citrus fruits such as lime, lemon, grapefruit, and orange.

Dextrin

The polysaccharide-based gelling agent may be dextrin. "Dextrin" refers to a group of low-molecular-weight carbohydrates produced by the hydrolysis of starch or glycogen. Dextrin is a mixture of polymers of D-glucose units linked by α-(1→4) or α-(1→6) glycosidic bonds.

Alginates

The polysaccharide-based gelling agent of the present invention may be alginate. "Alginate" refers to an anionic polysaccharide distributed widely in the cell walls of brown algae, where through binding with water, it forms a viscous gum. Alginate is a linear copolymer with homopolymeric blocks of (1-4)-linked β-D-mannuronate (M) and its C-5 epimer α-L-guluronate (G) residues, respectively, covalently link together in different sequences or blocks. Its color ranges from white to yellowish-brown. It is sold in filamentous, granular, or powdered forms.

Carrageenans

The polysaccharide-based gelling agent of the present invention may be a carrageenan. In some embodiments, carrageenan may provide particular advantages. "Carrageenan" refers to a family of polysaccharide gums extracted from red seaweed. They consist of linear sulfated high molecular weight polysaccharides made up of repeating galactose units and 3, 6 anhydrogalactose (3,6-AG), both sulfated and nonsulfated. The units are joined by alternating alpha 1-3 and beta 1-4 glycosidic linkages.

In some exemplary embodiments, the capsule shell 5 of the package 100 comprises both a modified starch and iota-carrageenan. In one embodiment, the weight ratio of the modified starch to the iota-carrageenan is at least about 1.5:1, with a preferred range being about 1.5:1 to about 4:1, or more preferably from about 2:1 to about 3:1. A gel forming composition with the above weight ratio is capable of fusion, under pressure, in the range of about 207 kPa to about 2070 kPa (about 30 to about 300 psi) and at temperatures in the range of from about 25 to about 80° C. In one embodiment, the capsule shell 5, according to the present invention, has a melting temperature of from about 2 to about 25° C., more preferably from about 3 to about 15° C. and most preferably about 4 to about 9° C. above its fusion temperature.

The iota-carrageenans may be preferably conformed to the specification laid down by the USA and European regulatory authorities. The iota-carrageenan is not degraded and should conform to minimum viscosity standards, which correspond to a molecular weight of about 100K Daltons. Standardized iota-carrageenans are preferred. A particular preferred standardized iota-carrageenan is commercially available from the FMC Corporation of Princeton, N.J., known as VISCARIN® SD389, standardized with 15% by weight dextrose. Other useful iota-carrageenans include a non-standardized iota-carrageenan from SKW BioSystems of Baupt, France known as XPU-HGI and a non-standardized iota-carrageenan from FMC.

The iota-carrageenan in these exemplary embodiments is used in an amount that, in combination with the modified starch, effectively causes the gel forming compositions to have the required gelatin-like functional properties. As those skilled in the art will appreciate, the gel has what is known as a wet shell composition and a dry shell composition. The dry shell composition results from the evaporation or removal of water from the wet shell composition during the manufacturing process for making the softgel capsule. The dry shell composition may still contain some water. Preferred amounts of iota-carrageenan range from about 6-12% by weight of the wet shell composition. More preferred amounts of iota-carrageenan range from about 7-12% by weight of the wet shell composition. Particularly preferred compositions contain about 9-11 weight % of iota-carrageenan, based on the weight of the wet shell composition. Even more preferred compositions contain about 10 weight % of iota-carrageenan by weight of the wet shell composition.

In some other exemplary embodiments, the capsule shell 5 is formed from only one gelling agent, which is gelatin. Preferably, the gelatin is mammalian gelatin. The capsule shell 5 typically contains between about 25-45% by weight of gelatin. Such gelatin-based gel is strong enough to survive manipulation in the encapsulation machine, provide good sealing properties at temperatures below the melting point of the film, and have sufficient elasticity to allow for the formation of the package 100.

The capsule shell 5 of the package 100 may further comprise at least one optional component selected from a plasticizer, a preservative, a flavoring agent, an opacifying agent, a buffer, an embrittlement inhibiting agent, a colorant, a disintegrant, a perfume, a flavoring, a shell texturing ingredient and/or pearlescent and/or glittering pigment, and water.

The plasticizers include glycerol, polyglycerol, glycerin, propylene glycol, polyethylene glycol, xylitol, sorbitol, non-crystalizing solutions of sorbitol, glucose, fructrose, and glucose syrups. These plasticizers may be used alone or in combination with each other. In a combination of plasticizers including glycerol, the glycerol typically comprises at least 30% by weight of the combination, normally in the range of about 30-70% by weight. One alternative combination is ANIDRISORB (a proprietary mixture of Sorbitol, Sorbitans, Maltitol, and Mannitol, available from Roquette Freres). Other plasticizers include saccharides and polysaccharides. The saccharides and polysaccharides suitable for use as a plasticizer herein may be produced by hydrolysis and/or hydrogenation of a simple or complex polysaccharides.

Where plasticizers are employed, they can be used in amounts of up to about 60% by weight of the dry shell composition or up to about 30% by weight of the wet shell composition used to make the capsule. More preferred compositions contain from about 10% to about 25% by weight, based on the weight of the wet shell composition and from about 30% to about 50% by weight of the dry shell composition.

Optionally, the capsule shell 5 may contain a preservative. Preservatives may be antimicrobial preservatives, which inhibit the growth of microbes, or they can be antioxidants such as oxygen absorbers, which inhibit the oxidation of fill within the package 100. Common antimicrobial preservatives include sorbic acid and its salts, benzoic acid and its salts, calcium propionate, sodium nitrite, sulfites (sulfur dioxide, sodium bisulfite, potassium hydrogen sulfite, etc.), and disodium ethylenediaminetetraacetic acid (EDTA). Antioxidants include butylated hydroxyanisole (BHA), butylated hydroxytoluene (BHT), tert -butylhydroquinone (TBHQ) and propyl gallate. Other preservatives include ethanol and methylchloroisothiazolinone.

Without preservatives, the wet capsule composition may be spoiled by microbial growth in a day or two. On a commercial scale, however, preservatives may not be needed because the wet ribbon would be quickly processed through the encapsulation machines and then the dryers. The dried capsule shell 5 does not support microbial growth.

In some embodiments, the capsule shell 5 may lose ductility during storage or shelf life, making it brittle. An embrittlement inhibiting agent may be added, which may be a mixture of sorbitol and one or more sorbitans. See U.S. Pat. No. 4,780,316, which is incorporated herein by reference.

In some embodiments, a buffer system may be used in the composition for forming capsule shell 5. Any known buffer can be used, with phosphate buffers being preferred. Controlling the pH of the composition may be highly important in some embodiments as carrageenans are rapidly broken down in conditions of acidity.

The fill materials for the soft package 100 may be any of a wide variety of materials suitable for encapsulation, including oils, hydrophilic liquids, and emulsions, silicone based serums. The fill material may be liquid, semi-solid, or suspension. The active components that may be contained within the oils and emulsions are hydrophobic and hydrophilic actives. Those skilled in the art are familiar with and will recognize suitable fill materials.

The package can be used for delivery of a multitude of products as fill materials from the package. Such products include, but are not limited to, cosmetics such as perfumes and serums, foods, hygiene products, medical devices, nutritional supplements, household products such as cleaning products, deodorizing products, polishing products, flavorings, veterinary medicines or other animal health products, and pharmaceuticals. From a regulatory perspective, the packages 100 are medical devices, which are regulated as a specific class of products.

The package 100 may be produced by fusing two different pieces of gel to form the capsule shell 5. The fusion of the two pieces of gel is performed by subjecting the gel to sufficient pressure and/or elevated temperature. The temperature at which fusion of two opposing films occurs should be below the melting point of the film, i.e., the fusion or sealing temperature is less than the melting point of the film composition.

A traditional technology for manufacturing the package 100 is the rotary die process for producing soft capsules in a continuous softgel capsule manufacturing process. Rotary die manufacture of softgel capsules is disclosed in detail in Ebert, W. R., "Soft elastic gelatin capsules: a unique dosage form", Pharmaceutical Tech., October 1977; Stanley, J. P., "Soft Gelatin Capsules", in The Theory and Practice of Industrial Pharmacy (Lachman, Lieberman and Kanig, Editors), 3rd Edition, published by Lea & Febiger, U.S. Pat. Nos. 1,970,396; 2,288,327; and 2,318,718. A good description of gelatin encapsulation techniques can also be found in WO 98/42294.

The packages 100 made by using the rotary die process typically have capsule shell thicknesses varying from about 0.024 cm to about 0.1778 cm, preferably from about 0.0350 cm to about 0.0508 cm and more preferably from about 0.0406 cm to about 0.0508 cm. The areas of reduced thickness 3 of capsule shell 5 will typically be from about 30% to about 70% thinner than other portions of capsule shell 5, and more preferably from about 40% to about 50% thinner than other portions of capsule shell 5.

In the method of the present invention, the areas of reduced thickness 3 may be formed by adaptation of one or more of the die used to form the capsule shell 5 to form an area of reduced thickness 3. Thus, the flexible ribbon of gel material fed to the die may be modified by the die to provide one or more areas of reduced thickness 3 during the manufacturing process. In this manner, the softgel capsules of the invention may be manufactured in a continuous manner while providing the desired one or more areas of reduced thickness 3 to the capsule shell 5 to permit opening of the package 100 by application of a compressive force as described above.

Other suitable methods of forming areas of reduced thickness 3 may also be employed. For example, the flexible ribbon of capsule shell material fed to the rotary die may be provided with one or more areas of reduced thickness in the ribbon prior to feeding the ribbon to the rotary die used to form the capsule shell 5. Alternatively, capsule shell 5 could be scored after manufacture of capsule shell 5 to provide an area of reduced thickness 3. In a preferred embodiment, the area of reduced thickness 3 is located in a decreased land area between two protrusions 2 forming the cat ear shape of FIG. 3D.

The invention also includes a method for manufacturing the package (100). In the method, a fill composition is provided between two pieces of softgel material. The two pieces of softgel material are then fused together using known techniques to form a softgel capsule encapsulating the fill composition. Finally, at least one area of reduced thickness (3) is created on a capsule shell (5) of the softgel capsule prior to or during said fusing step. The area of reduced thickness is maintained throughout the drying and hardening of the capsule.

The packages 100 may be stored and dried in a special cabinet with fans that produce a constant air flow in the cabinet. The drying process is typically performed for a period from one to eight hours, preferably from two to about six hours, more preferably from three to about four hours. During this drying period, the packages 100 reach a hardness of squeezable packages. The package's hardness is in a range of from 0.5N to about 3N, preferably from 1N to about 2.5N, and more preferably from 1.5N to about 2N.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A softgel capsule package for delivering a single-dose product, comprising:
    a softgel capsule shell formed from at least one gelling agent selected from a protein and a polysaccharide,
    the softgel capsule shell consisting of:
    an area having a first shell thickness,
    said area having the first shell thickness being oblong-shaped and having two protrusions that define a border, and
    one or more areas of reduced shell thickness relative to said first shell thickness, the one or more areas of reduced shell thickness being located within the border defined by the two protrusions;
    the one or more areas of reduced shell thickness being configured to rupture by exertion of a compression force on the oblong-shaped portion of the softgel capsule shell to provide an opening in the one or more areas of reduced thickness of the capsule shell through which the product contained in the package can be dispensed, and said opening in the one or more areas of reduced thickness of the capsule shell is limited by the border defined by the two protrusions.

2. The package of claim 1, wherein the one or more areas of reduced thickness comprise a deepest point in said shell between said protrusions.

3. The package of claim 2, wherein the one or more or areas of reduced thickness are convex relative to an area inside of said package and adjacent to said one or more areas of reduced thickness.

4. The package of claim 3, wherein the two protrusions are concave relative to an area inside of said package and adjacent to said one or more areas of reduced thickness.

5. The package of claim 1, wherein the protrusions are configured to create a back pressure on said one or more areas of reduced thickness.

6. The package of claim 1, wherein the one or more areas of reduced thickness are from about 30% to about 70% thinner than the first thickness of the capsule shell.

7. The package of claim 1, wherein the protrusions and the one or more areas of reduced thickness are configured to dispense the product as a spray.

8. The package of claim 7, wherein the softgel capsule shell has two or more areas of reduced thickness such that the spray is dispensed as a plurality of streams.

9. The package of claim 1, wherein said one or more areas of reduced thickness are sized to provide a desired dispensing.

10. The package of claim 1, wherein said package is biodegradable.

11. The package of claim 1, wherein the one or more areas of reduced thickness are circular, or linear.

12. The package of claim 1, wherein each said protrusion extends less than about 0.5 mm from the area of the shell having the first thickness.

13. The package of claim 1, wherein the softgel capsule package has an internal volume of from about 0.05 to about 5 ml.

14. The package of claim 1, wherein at least one said gelling agent is a protein-based gelling agent selected from the group consisting of collagen, gelatin, egg whites, and milk-based proteins.

15. The package of claim 1, wherein at least one said gelling agent is a polysaccharide-based gelling agent selected from the group consisting of cellulose-based materials, starches, modified starches, pectins, gums, dextrins, alginates, carrageenans and mixtures thereof.

16. The package of claim 1, where at least one said gelling agent is gelatin and the gelatin comprises from about 25% to about 45% by weight of a total weight of the softgel capsule shell.

17. The package of claim 1, further comprising an air hole located in a central area of the package.

* * * * *

UNITED STATES PATENT AND TRADEMARK OFFICE
CERTIFICATE OF CORRECTION

PATENT NO. : 10,898,438 B2
APPLICATION NO. : 15/587522
DATED : January 26, 2021
INVENTOR(S) : Baruzzi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 77 days.

Signed and Sealed this
Tenth Day of January, 2023

Katherine Kelly Vidal
*Director of the United States Patent and Trademark Office*